United States Patent [19]
Forsberg

[11] 4,322,479
[45] Mar. 30, 1982

[54] MAGNESIUM OXIDE-CARBOXYLATE COMPLEXES, METHOD FOR THEIR PREPARATION, AND COMPOSITIONS CONTAINING THE SAME

[75] Inventor: John W. Forsberg, Mentor-On-The-Lake, Ohio

[73] Assignee: The Lubrizol Corporation, Wickliffe, Ohio

[21] Appl. No.: 183,674

[22] Filed: Sep. 2, 1980

Related U.S. Application Data

[60] Division of Ser. No. 13,508, Feb. 21, 1979, Pat. No. 4,253,976, which is a continuation-in-part of Ser. No. 882,511, Mar. 1, 1978, abandoned, which is a division of Ser. No. 760,315, Jan. 18, 1977, Pat. No. 4,094,801, which is a continuation-in-part of Ser. No. 681,627, Apr. 29, 1976, abandoned.

[51] Int. Cl.$^3$ ............................................... B35B 9/00
[52] U.S. Cl. ..................................... 428/471; 428/470
[58] Field of Search ................... 428/471, 470; 252/33

[56] References Cited

U.S. PATENT DOCUMENTS

| | | | |
|---|---|---|---|
| 2,616,904 | 11/1952 | Asseff et al. | 252/33 |
| 4,094,801 | 6/1978 | Forsberg | 252/33 |
| 4,253,976 | 3/1981 | Forsberg | 252/33 |

FOREIGN PATENT DOCUMENTS

| | | | |
|---|---|---|---|
| 2718780 | 11/1977 | Fed. Rep. of Germany | 252/33 |
| 789820 | 1/1958 | United Kingdom | 252/33 |
| 1005957 | 9/1965 | United Kingdom | 44/51 |
| 1052380 | 12/1966 | United Kingdom | 252/33 |
| 1054280 | 1/1967 | United Kingdom | 252/33 |

*Primary Examiner*—George F. Lesmes
*Assistant Examiner*—E. Rollins Buffalow
*Attorney, Agent, or Firm*—Ronald L. Lyons; John P. Ward; William H. Pittman

[57] ABSTRACT

Thixotropic magnesium-containing complexes are prepared by heating a mixture of magnesium hydroxide, magnesium oxide, hydrated magnesium oxide or a magnesium alkoxide; a carboxylic acid, a mixture thereof with a sulfonic or pentavalent phosphorus acid, or an ester or salt of either of these; water (optional under certain conditions); and an organic solubilizing agent (which may be liquid or solid at ambient temperature) for the acid or ester. The amount of magnesium is such as to provide a basic composition. The resulting complexes may be obtained in liquid or solid form, and are useful as additives for lubricants and fuels and as protective coating compositions for metal surfaces (such as automotive undercoats and frame coatings).

15 Claims, No Drawings

MAGNESIUM OXIDE-CARBOXYLATE COMPLEXES, METHOD FOR THEIR PREPARATION, AND COMPOSITIONS CONTAINING THE SAME

RELATED APPLICATIONS

This application is a division of copending application Ser. No. 13,508, filed Feb. 21, 1979 now U.S. Pat. No. 4,253,976. Said application is a continuation-in-part of application Ser. No. 882,511, filed Mar. 1, 1978, now abandoned, which is a division of application Ser. No. 760,315, filed Jan. 18, 1977, now U.S. Pat. No. 4,094,801, which in turn is a continuation-in-part of application Ser. No. 681,627, filed Apr. 29, 1976, now abandoned.

INTRODUCTION AND SUMMARY OF THE INVENTION

This invention relates to new magnesium-containing compositions of matter and methods for their preparation. In a general sense, the invention comprises thixotropic noncarbonated magnesium-containing complexes which are prepared by heating, at a temperature above about 30° C., a mixture comprising:

(A) At least one of magnesium hydroxide, magnesium oxide, hydrated magnesium oxide and a magnesium alkoxide;

(B) At least one oleophilic organic reagent comprising a carboxylic acid, a mixture of a major amount thereof with a minor amount of a sulfonic acid or pentavalent phosphorus acid, or an ester or alkali metal or alkaline earth metal salt of either of these;

(C) Water, if necessary to convert a substantial proportion of component A to magnesium hydroxide or hydrated magnesium oxide; and (D) At least one organic solubilizing agent for component B;

the ratio of equivalents of magnesium to the acid portion of component B being at least about 5:1; and the amount of water present, if any, being sufficient to hydrate a substantial proportion of component A calculated as magnesium oxide.

Several methods are known for the preparation of basic magnesium compounds for use in lubricants, greases and the like. For example, U.S. Pat. No. 3,865,737 describes the formation of a highly basic magnesium-containing liquid dispersion by mixing an oil-soluble dispersing agent, magnesium oxide, a volatile aliphatic hydrocarbon solvent, alcohol, water and ammonia or an ammonium compound, treating the mixture with carbon dioxide, adding a non-volatile diluent oil and removing volatiles. Similarly, U.S. Pat. No. 3,629,109 describes the carbonation of a mixture of an oil-soluble organic acid or salt thereof, magnesium oxide, a lower aliphatic alcohol, water and an organic liquid diluent. The products obtained by these methods may be characterized, for the most part, as basic oleophilic magnesium carbonates since an essential step in their preparation is reaction with carbon dioxide.

In accordance with the present invention, it has been discovered that highly basic, thixotropic magnesium complexes may be prepared without reaction with carbon dioxide or similar acidic gases. The products obtained in accordance with the present invention, which may be characterized as complexes of magnesium oxide or hydroxide and a magnesium salt of the acid comprising component B, and which are hereinafter sometimes referred to merely as "magnesium complexes", have a wide variety of uses, including additives for lubricants and fuel oils and corrosion-resistant coatings or constituents thereof.

A principal object of the present invention, therefore, is to provide new oleophilic magnesium-containing compositions and a method for their preparation.

A further object is to provide a method for producing magnesium complexes which does not necessitate reaction with carbon dioxide or a similar acidic gas.

A further object is to provide basic thixotropic magnesium compositions which may be obtained either in liquid or solid form.

Still another object is to provide thixotropic magnesium-containing compositions useful as greases, as detergent additives for lubricants or as corrosion inhibitors, vanadium scavengers and smoke suppressants for fuels, and in the formulation of corrosion-resistant coatings for metals.

Other objects will in part be obvious and will in part appear hereinafter.

COMPONENT A

Component A used in the method of this invention is magnesium hydroxide, magnesium oxide, hydrated magnesium oxide, a magnesium alkoxide, or a mixture of these. Magnesium hydroxide and magnesium oxide are, of course, represented by the formulas $Mg(OH)_2$ and $MgO$, respectively. Magnesium oxide exists in an inactive "dead burned" and a hydratable "reactive" form and the latter is the one which is useful in this invention although mixtures of the "reactive" form with minor amounts of the "dead burned" form may also be used. "Hydrated magnesium oxide", for the purpose of this invention, is magnesium oxide which is associated with water in an amount less than that required for conversion to magnesium hydroxide; that is, the amount of water is less than one mole per mole of magnesium oxide. As so defined, "hydrated magnesium oxide" may actually be a mixture of various proportions of magnesium oxide and magnesium hydroxide and its exact chemical nature is not critical to this invention. Typically, the amount of water present in "hydrated magnesium oxide" is at least about 0.7 mole per mole of the oxide.

The magnesium alkoxides, especially the lower alkoxides (i.e., those in which the alkyl groups contain 7 carbon atoms or less), are equivalent to magnesium oxide and hydroxide for the purpose of this invention; they are hydrolyzed by water to magnesium hydroxide under the conditions described hereinafter.

The equivalent weight of component A is half its molecular weight, since magnesium is a divalent element.

COMPONENT B

Component B is at least one oleophilic reagent comprising a carboxylic acid or a mixture thereof with a sulfonic acid, or salts or esters thereof. These acids include many of those known to be susceptible to overbasing and especially many of those disclosed in a number of U.S. Pat. Nos. such as 2,616,904; 2,695,910; 3,312,618; 3,746,643; 3,764,533; and the aforementioned U.S. Pat. No. 3,629,109. Those patents are incorporated by reference herein for their disclosure of suitable acidic oleophilic reagents.

The carboxylic acids suitable for use as component B include aliphatic, cycloaliphatic and aromatic mono- and polybasic carboxylic acids free from acetylenic unsaturation, including naphthenic acids, alkyl- or alkenyl-substituted cyclopentanoic acids, alkyl- or alkenyl-substituted cyclohexanoic acids, and alkyl- or alkenyl-substituted aromatic carboxylic acids. The aliphatic acids generally contain from about 8 to about 50, and preferably from about 12 to about 25, carbon atoms. The cycloaliphatic and aliphatic carboxylic acids are preferred and they can be saturated or unsaturated. Specific examples include 2-ethylhexanoic acid, linolenic acid, propylene tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentanecarboxylic acid, myristic acid, dilauryldecahydronaphthalenecarboxylic acid, stearyl-octahydroindenecarboxylic acid, palmitic acid, alkyl- and alkenyl-succinic acids, acids formed by oxidation of petrolatum or of hydrocarbon waxes, and commercially available mixtures of two or more carboxylic acids such as tall oil acids, rosin acids, and the like.

The above-described carboxylic acids may be used in admixture with a minor amount of a sulfonic or pentavalent phosphorus acid; that is, component B may comprise a mixture containing more than 50% by weight of carboxylic acids and less than 50% of sulfonic or pentavalent phosphorus acids. Suitable sulfonic acids include those represented by the formulas $R^1(SO_3H)_r$ and $(R^2)_xT(SO_3H)_y$. In these formulas, $R^1$ is an aliphatic or aliphatic-substituted cycloaliphatic hydrocarbon or essentially hydrocarbon radical free from acetylenic unsaturation and containing up to about 60 carbon atoms. When $R^1$ is aliphatic, it usually contains at least about 15 carbon atoms; when it is an aliphatic-substituted cycloaliphatic radical, the aliphatic substituents usually contain a total of at least about 12 carbon atoms. Examples of $R^1$ are alkyl, alkenyl and alkoxyalkyl radicals, and aliphatic-substituted cycloaliphatic radicals wherein the aliphatic substituents are alkyl, alkenyl, alkoxy, alkoxyalkyl, carboxyalkyl and the like. Generally, the cycloaliphatic nucleus is derived from a cycloalkane or a cycloalkene such as cyclopentane, cyclohexane, cyclohexene or cyclopentene. Specific examples of $R^1$ are cetylcyclohexyl, laurylcyclohexyl, cetyloxyethyl, octadecenyl, and radicals derived from petroleum, saturated and unsaturated paraffin wax, and olefin polymers including polymerized monoolefins and diolefins containing about 2–8 carbon atoms per olefinic monomer unit. $R^1$ can also contain other substituents such as phenyl, cycloalkyl, hydroxy, mercapto, halo, nitro, amino, nitroso, lower alkoxy, lower alkylmercapto, carboxy, carbalkoxy, oxo or thio, or interrupting groups such as —NH—, —O— or —S—, as long as the essentially hydrocarbon character thereof is not destroyed.

$R^2$ is generally a hydrocarbon or essentially hydrocarbon radical free from acetylenic unsaturation and containing from about 4 to about 60 aliphatic carbon atoms, preferably an aliphatic hydrocarbon radical such as alkyl or alkenyl. It may also, however, contain substituents or interrupting groups such as those enumerated above provided the essentially hydrocarbon character thereof is retained. In general, the non-carbon atoms present in $R^1$ or $R^2$ do not account for more than 10% of the total weight thereof.

The radical T is a cyclic nucleus which may be derived from an aromatic hydrocarbon such as benzene, naphthalene, anthracene or biphenyl, or from a heterocyclic compound such as pyridine, indole or isoindole. Ordinarily, T is an aromatic hydrocarbon nucleus, especially a benzene or naphthalene nucleus.

The subscript x is at least 1 and is generally 1–3. The subscripts r and y have an average value of about 1–4 per molecule and are generally also 1.

Illustrative sulfonic acids useful as part of component B are mahogany sulfonic acids, petrolatum sulfonic acids, mono- and polywax-substituted naphthalene sulfonic acids, cetylchlorobenzene sulfonic acids, cetylphenol sulfonic acids, cetylphenol disulfide sulfonic acids, cetoxycapryl benzene sulfonic acids, dicetyl thianthrene sulfonic acids, dilauryl β-naphthol sulfonic acids, dicapryl nitronaphthalene sulfonic acids, paraffin wax sulfonic acids, unsaturated paraffin wax sulfonic acids, hydroxy-substituted paraffin wax sulfonic acids, tetraisobutylene sulfonic acids, tetra-amylene sulfonic acids, chloro-substituted paraffin wax sulfonic acids, nitroso-substituted paraffin wax sulfonic acids, petroleum naphthene sulfonic acids, cetylcyclopentyl sulfonic acids, lauryl cyclohexyl sulfonic acids, mono- and polywax-substituted cyclohexyl sulfonic acids, post-dodecylbenzene sulfonic acids, "dimer alkylate" sulfonic acids, and the like. These sulfonic acids are well-known in the art and require no further discussion herein.

The pentavalent phosphorus acids useful as part of component B may be represented by the formula

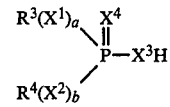

wherein each of $R^3$ and $R^4$ is hydrogen or a hydrocarbon or essentially hydrocarbon radical preferably having from about 4 to about 25 carbon atoms, at least one of $R^3$ and $R^4$ being hydrocarbon or essentially hydrocarbon; each of $X^1$, $X^2$, $X^3$ and $X^4$ is oxygen or sulfur; and each of a and b is 0 or 1. Thus, it will be appreciated that the phosphorus acid may be an organophosphoric, phosphonic or phosphinic acid, or a thio analog of any of these.

Usually, the phosphorus acids are those of the formula

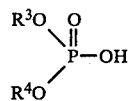

wherein $R^3$ is a phenyl radical or (preferably) an alkyl radical having up to 18 carbon atoms, and $R^4$ is hydrogen or a similar phenyl or alkyl radical. Mixtures of such phosphorus acids are often preferred because of their ease of preparation.

Also useful as component B are the alkali metal and alkaline earth metal salts (e.g., sodium, potassium, magnesium, calcium, strontium or barium salts, with magnesium salts being preferred) and esters of the acids previously described. The suitable esters include those with monohydric alcohols free from acetylenic unsaturation and having from about 1 to about 25 carbon atoms, including monohydric alcohols such as methanol, ethanol, the butanols, the hexanols, allyl alcohol, crotyl alcohol, stearyl alcohol and oleyl alcohol, and polyhydric alcohols such as ethylene glycol, diethylene glycol, propylene glycol, glycerol, sorbitol, sorbitan and similar carbohydrates and derivatives of carbohydrates.

It will be appreciated from the above description of component B that it comprises an organic acid or a compound hydrolyzable thereto. The ratio of equivalents of magnesium to equivalents of acid is important in the context of the invention, and so the equivalent weight of the acid portion of component B must be defined.

Obviously, to the extent that component B is a free acid its equivalent weight is its molecular weight divided by the number of acidic groups present per molecule. To the extent component B is an ester or salt of a carboxylic or sulfonic acid, it is considered to be convertible to the free acid during the reaction with component A and water and its equivalent weight is similarly calculated. To the extent that component B is a phosphorus acid or a salt or ester thereof, its equivalent weight is its molecular weight divided by the sum of the acidic hydroxy groups bonded to phosphorus (or salts thereof) and the number of ester groups hydrolyzable to such hydroxy groups (or salts thereof) under the reaction conditions of the invention. If any ester groups remain unhydrolyzed, the ester is considered inert to that extent for the purpose of calculating equivalent weight.

The preferred compounds for use as component B are the above-described carboxylic acids having an equivalent weight between about 200 and about 500 and mixtures thereof with sulfonic acids of similar molecular weight, especially alkylaromatic sulfonic acids and more particularly alkylbenzenesulfonic acids.

One of the characteristics of component B is that it is oleophilic. This means that it is soluble or at least stably dispersible (as defined hereinafter) in oil or similar non-polar organic liquids such as hexane, naphtha, Stoddard solvent, benzene, toluene and the like. While component B need not be oil-soluble, the oil-soluble acids are preferred for the purposes of this invention. These oil-soluble compounds constitute a known subgenus of the previously described compounds useful as component B.

COMPONENT C

Component C is water, which may be used in the liquid or vapor phase and is under certain conditions optional (as described hereinafter). For the purpose of the present invention, the equivalent weight of water is considered to be 9 (half its molecular weight).

COMPONENT D

Component D is at least one organic solubilizing agent for component B. It may be solid or liquid at room temperature, although liquids are often preferred. It need not be a solvent for component B, in the sense that component B is entirely soluble therein when in the liquid state, but should be at least a partial solvent in the sense that relatively small proportions of component B, at least, when blended with component D in the liquid state will form a homogeneous mixture.

Materials useful as component D include substantially inert, normally liquid organic diluents. The term "substantially inert" as used herein is intended to mean that the diluent is inert to chemical or physical change under the conditions in which it is used so as not to materially interfere in an adverse manner with the preparation, storage, blending and/or functioning of the magnesium complex in the context of its intended use. For example, small amounts of a diluent can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is thus readily understood and appreciated by those of ordinary skill in the art.

Among the preferred normally liquid diluents are non-polar compounds or mixtures of compounds such as naphtha, hexane, kerosene, mineral oil, Stoddard solvent, benzene, toluene, xylene, low molecular weight polybutenes, and alkylbenzenes of the type present as unsulfonated residue in alkylbenzenesulfonic acids. Also suitable are somewhat more polar liquids such as 1-butanol, 2-butanol, ethylene glycol, propylene glycol, ethylene glycol monomethyl ether, ethylene glycol monobutyl ether, ethylene glycol dimethyl ether, diethylene glycol and its ethers, wax-derived alcohol mixtures, methyl ethyl ketone, chlorobenzene, pyridine, indole, furan and tetrahydrofuran.

Also useful are substantially inert materials which are solid at ambient temperature, and which may be chemically similar to the above-described liquids. These include the following:

1. Waxes, such as:
   Crystalline (including microcrystalline) wax
   Paraffin wax
   Petrolatum wax
   Beeswax
   Bohemia wax
   Hydrogenated castor oil
   Lanolin
   Shellac wax
   Spermaceti
   Carnauba wax
   Candelilla wax
   Chlorinated naphthalene
   Waxy alcohol mixtures (e.g., $C_{20-40}$ aliphatic alcohols)
   Other waxy materials of the type disclosed in Kirk-Othmer, *Encyclopedia of Chemical Technology*, Second Edition, vol. 22, pp. 156–173 (which is incorporated by reference herein for such disclosure)
2. Hydrocarbon and similar resins, such as:
   Olefin polymer resins and waxes (e.g., polyethylene, polypropylene)
   Terpene resins
   Coumarone-indene resins
   Phenolic and alkylated phenolic resins
   Furan resins
3. Natural resins, such as:
   Copal
   Manila chips
   Gum damar
   Accroides gum
   Rosin
   Hydroabietyl alcohol resin
4. Addition polymer resins, such as:
   Styrene-butadiene
   Hydrogenated styrene-butadiene
   Polystyrene and poly($\alpha$-methylstyrene)
   Olefin-vinyl acetate copolymers Polyvinyl acetate
Polyvinyl chloride
Vinyl acetate-vinyl chloride copolymers
Acrylic resins
Solid polybutenes
5. Polyester resins
6. Solid plasticizers, such as:
Triethylene glycol dibenzoate
Neopentyl glycol dibenzoate
Glyceryl tribenzoate It is also within the scope of the invention to use mixtures of any of the materials described above. Such mixtures may be of materials all of which are liquid at normal ambient temperatures (e.g., about 20°–30° C.), such as mineral oil-toluene, Stoddard solvent-toluene, mineral oil-alkylbenzene, Stoddard solvent-alkylbenzene; of materials all of which are solid at normal ambient temperatures, such as paraffin wax-polyethylene wax, paraffin wax-polyethylene wax-$C_{20-40}$ alcohol wax; or of materials which are both liquid and solid at normal ambient temperatures, such as mixtures of the above-mentioned normally liquid diluents and a resin or hydrocarbon wax (e.g., paraffin wax-toluene, polypropylene-toluene, polypropylene-mineral oil).

COMPONENT PROPORTIONS

The relative proportions of components A, B, C and D are an important feature of this invention since the physical state in which the magnesium complex is obtained depends to a great extent on the proportions of the components used for their preparation.

As previously noted, the ratio of equivalents of magnesium to the acid portion of component B is at least about 5:1. This ratio is hereinafter sometimes referred to as the "magnesium ratio". (It will be appreciated that the magnesium ratio is such as to produce a basic magnesium complex.) If component B is a free carboxylic acid or an ester or salt thereof with a metal other than magnesium, the ratio of component A to component B will be identical to the magnesium ratio. If component B is a magnesium salt, the ratio of component A to component B will be somewhat less than the magnesium ratio since part of the magnesium is provided by component B.

It has been found that magnesium complexes with relatively low magnesium ratios (e.g., from about 5:1 to about 21:1 and particularly from about 5:1 to about 10:1) are particularly useful as lubricant additives. Complexes with a magnesium ratio above about 60:1 and preferably up to about 150:1 find utility principally as additives for fuel oils. As protective coatings for metals, it is preferred to employ complexes in which component D is entirely or predominantly liquid and the magnesium ratio is between about 25:1 and about 60:1, or solid (e.g., "hot melt") complexes in which component D is entirely or predominantly solid at ambient temperature and which typically have a magnesium ratio from about 5:1 to about 50:1.

The ratio of moles of water (component C) to gram-atoms of magnesium in component A (said ratio hereinafter sometimes designated the "water ratio") is also critical. When component A is substantially all magnesium hydroxide or hydrated magnesium oxide, the presence of water is frequently not required. If water is not present, however, complex preparation usually requires extremely efficient high-speed mixing (e.g., by mixers such as that sold under the trade name "Dispersator" by Premier Mill Corporation) so as to produce a uniform product. When a substantial portion of component A is magnesium oxide or a magnesium alkoxide, the presence of water as component C is required.

Most often, the use of water is advantageous regardless of the identity of component A. When it is present, the amount of water should be at least sufficient to hydrate a substantial proportion of component A, calculated as magnesium oxide. The proportion of additional water over and above that amount will depend on the nature of the product desired and the intended use thereof. If component A is anhydrous magnesium oxide the water ratio should generally be at least about 0.7:1 so as to produce a substantial proportion of the hydrated magnesium oxide referred to hereinabove.

A water ratio up to about 3.0:1, and especially from about 0.7:1 to about 3.0:1, is usually adequate to produce a composition of this invention. If larger amounts of water than this are used, it is frequently possible to remove excess water, at least some of which separates from the magnesium complex as a separate layer and the remainder of which can be removed by azeotropic distillation or the like. More water may be desirable for the preparation of the complex in certain instances; for example, magnesium oxide frequently contains traces of sodium compounds whose presence may be undesirable in the complex, and if so, such compounds may be removed by using up to about 8 moles of water per mole of component A and removing the excess, which has dissolved therein the sodium compounds. When the excess water has been removed, the molar ratio of remaining water to component A is usually below about 3:1 as noted above.

As among various magnesium complexes with water ratios between about 0.7:1 and about 3.0:1, those having a water ratio below about 1:1 are often particularly useful as lubricant additives or fuel oil additives, while those having a somewhat higher water ratio (e.g., between about 1:1 and 3:1) may be particularly useful in the preparation of corrosion-resistant coating compositions.

The ratio of component D to component A is not critical and may be varied so as to provide magnesium complexes suitable for the particular use for which they are intended. For example, a complex suitable as a lubricant additive may frequently be obtained by employing as component D solely the unsulfonated alkylbenzene present as an impurity in the sulfonic acid used as component B. In that event, the weight ratio of component D to component A will usually be below about 1:1 and frequently as low as 0.5–0.7:1. In general, when a lubricant additive product is desired it is inadvisable to use volatile materials as component D.

When the magnesium complex is to be used as a fuel oil additive, higher amounts of component D are frequently preferred and these may include relatively volatile materials such as toluene or xylene, less volatile materials such as mineral oil or mineral seal oil, and mixtures of volatile and less volatile materials. The proportions of volatile and non-volatile solubilizing agents in such mixtures are subject to wide variation, but in any event it is usually found that the total weight ratio of component D to component A should be from about 1.2:1 to about 1.8:1.

When a product useful in a protective metal coating is desired, still higher ratios (e.g., from about 2:1 to about 3:1) are often employed with one of the solubilizing agents being a substantially volatile aliphatic hydrocarbon such as naphtha or Stoddard solvent, and the other being a somewhat less volatile material such as mineral oil. Another useful type of complex for metal coating is the solid (e.g., "hot melt") type briefly referred to hereinabove, in which component D comprises mostly or entirely materials which are solid at ambient temperature, in which case the ratio of D to A may be between about 0.5:1 and about 6:1.

PREPARATION OF THE MAGNESIUM COMPLEX

The magnesium complexes of this invention are prepared by merely blending the components described hereinabove and heating the resulting blend at a temperature above about 30° C. It is important that water (if present as component C) remain in the blend during substantially the entire period of preparation of the magnesium complex, and the maximum temperature thereof should be adjusted accordingly. However, said water may be present in the liquid or vapor state, i.e., as liquid water or as steam, though it will be apparent to those skilled in the art that the preparation of complexes involving a relatively large amount of water will be difficult if not impossible, at least at atmospheric pressure, if the water is present as steam. Therefore, it is generally found that temperatures between about 30° and about 125° C. are most conveniently employed at atmospheric pressure, and the preparation should be carried out under superatmospheric pressure if the use of higher temperatures is likely. Most often, a maximum temperature of about 100° C. is convenient when component D is entirely or predominantly liquid and the preferred temperature range is then between about 40° and about 90° C. Naturally, the temperature may be somewhat higher (e.g., between about 95° and about 150° C.) when component D is entirely or predominantly a solid at ambient temperature.

The order of addition of the various components is not critical. It is often convenient to first combine components A, B and D and subsequently to add component C (water) either all at once or incrementally. It is also often found convenient to prepare an initial mixture containing only a relatively small portion of component A (e.g., from about 5% to about 10% of the total amount thereof) and to add the remainder at a later stage, typically during or after the addition of water. Finally, it is within the scope of the invention to prepare the magnesium complex using only a portion of the amount of component D intended, and to add the remainder after the complex has been prepared. The amount subsequently added is generally less than about 50% and preferably less than about 40% by weight of the total amount to be used. This subsequent addition of part of component D is most often useful when component D is partly or entirely solid (for example, when it comprises waxes and/or resins) and/or when it imparts additional desirable properties such as modifying fluidity under the conditions of use.

The magnesium complexes of this invention are thixotropic; that is, they decrease in viscosity when agitated and return to approximately their original viscosity after agitation ceases. When component D is predominantly liquid, the complexes are typically viscous liquids or heterogeneous dispersions in the form of greases or gels. When component D is predominantly solid, the magnesium complex may be a solid "hot melt" type material.

The solid materials are useful for many purposes, such as for the formation of corrosion-resistant coatings as described hereinafter. For some other applications, such as those involving lubricants and fuels, the complex is preferably obtained in the form of a relatively non-viscous, easily flowable liquid. Such liquids may be obtained by methods well known to those of skill in the art, such as by maximizing the amount of liquid diluent present as component D or by decreasing the relative amount of component A or component C in the reaction mixture. Alternatively, a viscous or solid complex can be further diluted with a substantially inert organic liquid diluent of the type described hereinabove to produce a homogeneous solution. One of the unique and desirable characteristics of the thixotropic compositions of this invention is their capability of existing either as heterogeneous compositions or homogeneous, relatively dilute solutions or dispersions.

A method which is sometimes advantageous for incorporating relatively large amounts of magnesium while making possible the formation of a homogeneous solution or dispersion in mineral oil or the like is to prepare the complex in the presence of ammonium hydroxide, which may be prepared from ammonia and the water present as component C. The amount of ammonium hydroxide required is small, generally less than about 10% by weight based on the water present. Insoluble materials can then be removed by diluting with a non-polar volatile organic liquid such as hexane or naphtha, centrifuging, and stripping the volatile liquid, or by equivalent means.

Another method for clarifying the magnesium complex for use in mineral oil, which may be employed in addition to or in place of preparation in the presence of ammonium hydroxide, is to add water or an acidic or basic reagent after preparation of the complex. The acidic or basic reagent may be organic or inorganic; suitable ones include sodium hydroxide, potassium hydroxide, ammonium hydroxide, triethanolamine, tartaric acid and citric acid. The amount of water or acidic or basic reagent is generally less than about 10% by weight of the magnesium complex system.

The stability of the magnesium complexes of this invention is often improved if a minor effective amount of an oxidation inhibitor is incorporated therein. Suitable oxidation inhibitors include the hindered phenol type, illustrated by 2,6-di-t-butylphenol and its derivatives; and the arylamine type, illustrated by phenyl-$\alpha$-naphthylamine. The amount of antioxidant required is usually between about 0.1% and about 2% and preferably between about 0.2% and 1% by weight. Oxidation inhibitors are particularly useful in the corrosion-resistant coating compositions of this invention since they inhibit viscosity decreases thereof.

The preparation of the magnesium complexes of this invention is illustrated by the following examples. All parts are by weight.

EXAMPLE 1

A mixture of 754 parts of water, 23 parts of magnesium oxide, 210 parts of mineral oil and 247 parts of Stoddard solvent is heated to about 40° C. and 331 parts of a carboxylic acid having an equivalent weight of about 350 and obtained by oxidation of petrolatum, which acid has been preheated to about 50°–60° C., is added as the temperature of the mixture is maintained at 40°–45° C. An additional 350 parts of magnesium oxide is added, with stirring, and the temperature of the mixture is increased to 75° C. An opaque dispersion is obtained which is screened to afford the desired magnesium oxide-carboxylate complex.

EXAMPLE 2

A product similar to that of Example 1 is prepared, substituting about 300 parts of sorbitan trioleate for the oxidized petrolatum.

EXAMPLE 3

A mixture of 16 parts of an alkylbenzenesulfonic acid having an equivalent weight of about 430 and containing about 22% unsulfonated alkylbenzene, 305 parts of mineral oil, 180 parts of magnesium oxide and 96 parts of "Hydrex 440", a mixture of hydrogenated fatty acids obtainable from Union Camp Corporation, is heated to 95° C. and blown with steam for two hours. The temperature is increased to 145°-150° C., an additional 28 parts of mineral oil is added and the mixture is blown with air as the temperature is heated to 170° C. over 15 minutes. The mixture is then cooled to room temperature and an additional 44 parts of mineral oil is added to yield the desired magnesium oxide-carboxylate-sulfonate complex having the consistency of a grease.

LUBRICANTS AND FUELS

When in the form of flowable liquids as previously described, the magnesium complexes of this invention are stably dispersible in the normally liquid media (e.g., oil, fuel, etc.) in which they are intended to function. Thus, for example, compositions intended for use in oils are stably dispersible in an oil in which they are to be used. The term "stably dispersible" as used in the specification and appended claims is intended to mean the magnesium complex or other material is capable of being dispersed in a given medium to an extent which allows it to function in its intended manner. Thus, for example, when a magnesium complex is used in an oil, it is sufficient that it be capable of being suspended in the oil in an amount sufficient to enable the oil to possess one or more of the desired properties imparted to it by the suspended complex. Such suspension can be achieved in various conventional ways. For example, in constantly circulating oil or oil in splash lubricating systems, physical agitation can keep the complex suspended in oil. Likewise, conventional dispersants (such as the acylated nitrogen dispersants disclosed in U.S. Pat. No. 3,219,666) often found in lubricating oils and fuels promote the stable dispersion or suspension of the magnesium complex. In any event, the complex will be "stably dispersible" in the normally liquid media in which it will be used in at least the minimum concentrations set forth elsewhere herein. Thus, the terminology "stably dispersible" is used in a conventional manner and will be understood by those of ordinary skill in the art.

As previously indicated, the magnesium complexes of this invention may be homogeneously incorporated into lubricants, in which they function primarily as ash-producing detergents. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebactate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerylthritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils and those obtained directly from a natural or synthetic source without further purification treatment. For example, a shale oil obtained directly from retorting operations, a petroleum oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the magnesium complex of this invention sufficient to impart detergency thereto. Normally this amount will be from about 0.05% to about 20%, preferably from about 0.5% to about 10%, of the total weight of the lubricant. In lubricating oils operated under extremely adverse conditions, such as lubricating oils for marine diesel engines, the magnesium complexes of this invention may be present in amounts up to about 30%.

The magnesium complexes of the present invention are also useful as corrosion inhibitors, vanadium scavengers and smoke suppressants in fuels. For that purpose, they are homogeneously incorporated in minor proportions in normally liquid fuels, usually hydrocarbonaceous fuels such as fuel oils, bunker fuels and the like. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of the invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated.

Generally, these fuel compositions contain an amount of the magnesium complex sufficient to impart corrosion resistance thereto, suppress smoke or serve as a vanadium scavenger; usually this amount is from about 1 to about 10,000, preferably from about 4 to about 1000, parts thereof by weight per million parts of fuel.

The invention also contemplates the use of other additives in combination with the magnesium complexes. Other additives useful in lubricants include, for example, auxiliary detergents and dispersants of the ash-producing or ashless type, corrosion- and oxidation-inhibiting agents, pour point depressing agents, extreme pressure agents, color stabilizers and anti-foam agents.

The auxiliary ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. Pat. Nos. including the following:

3,163,603
3,184,474
3,215,707
3,219,666
3,271,310
3,272,746
3,281,357
3,306,908
3,311,558
3,316,177
3,340,281
3,341,542
3,346,493
3,351,552
3,381,022
3,399,141

3,415,750
3,433,744
3,444,170
3,448,048
3,448,049
3,451,933
3,454,607
3,467,668
3,501,405
3,522,179
3,541,012
3,542,678
3,542,680
3,567,637
3,574,101
3,576,743
3,630,904
3,632,510
3,632,511
3,697,428
3,725,441
Re. 26,433

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:
3,275,554
3,438,757
3,454,555
3,565,804

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:
3,413,347
3,697,574
3,725,277
3,725,480
3,726,882

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:
3,036,003
3,087,936
3,200,107
3,216,936
3,254,025
3,256,185
3,278,550
3,280,234
3,281,428
3,282,955
3,312,619
3,366,569
3,367,943
3,373,111
3,403,102
3,442,808
3,455,831
3,455,832
3,493,520
3,502,677
3,513,093
3,533,945
3,539,633
3,573,010
3,579,450
3,591,598
3,600,372
3,639,242
3,649,229
3,649,659
3,658,836
3,697,574
3,702,757
3,703,536
3,704,308
3,708,522

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:
3,329,658
3,449,250
3,519,565
3,666,730
3,687,849
3,702,300

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite; diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Other additives useful in fuels include deposit preventers or modifiers such as triaryl phosphates, dyes, cetane improvers, antioxidants such as 2,6-di-tertiarybutyl-4-methylphenol, rust inhibitors such as alkylated succinic acids and anhydrides, bacteriostatic agents, gum inhibitors, metal deactivators, demulsifiers and the like.

The magnesium complexes of this invention can be added directly to the lubricant or fuel. Preferably, however, they are diluted with a substantially inert, normally liquid organic diluent such as those mentioned hereinabove, particularly mineral oil, naphtha, benzene, toluene or xylene, to form an additive concentrate. These concentrates generally contain about 20–90% by weight of the magnesium complex and may contain addition, one or more of the other additives described hereinabove.

CORROSION-RESISTANT COATINGS AND OTHER USES

The thixotropic magnesium complexes of this invention, especially those that are viscous or solid at ambient temperatures, are useful as corrosion-resistant coatings for metal (e.g., ferrous metal, galvanized, aluminum or magnesium) surfaces, especially in the nature of undercoats for automotive bodies, coatings for structural members such as automotive frames, and the like. They may be employed as such alone or in combination with various adjuvants known to be useful in such coatings, such as other basic metal sulfonates (of the type disclosed in U.S. Pat. No. 3,453,124, which is incorporated by reference herein for such disclosure), acidic phosphate esters, and waxes and resins as disclosed hereinabove with reference to component D.

For coating automotive frames and the like, a solid "hot melt" composition is suitable. Frequently, a dye or pigment is added to the "hot melt" composition.

For corrosion-inhibiting purposes, the viscous or solid composition of this invention may be applied to the metal surface by any ordinary method such as brushing, spraying, dip-coating, flow-coating, roller-coating and the like, with heating if necessary (as to liquefy a solid composition). The viscosity may be adjusted for the particular method of application selected by adding, if necessary, a diluent which may be a substantially inert, normally liquid organic diluent, an analogous solid, or a mixture of liquids and solids; suitable materials are described hereinabove with reference to component D. The coated metal surface may then be dried either by exposure to air or by baking, although drying frequently takes place without a separate drying step. If the coating composition is of a suitable viscosity to allow direct application to the metal surface, no solvent is used and no drying procedure need be followed. A more viscous grease can be diluted to produce a less viscous grease which is suitable for application as previously noted. The film thickness is not critical although a coating of about 50–2000 mg. per square foot of surface in the case of an undercoat, and up to about 10,000 mg. per square foot in the case of a coating for frames or other structural members, is usually sufficient to provide adequate protection. Heavier coatings can be used if desired, but they normally contribute little in the way of additional protection.

The magnesium complexes of this invention are also useful as lubricant greases and as stabilizers for resinous compositions, typically polyvinyl chloride, to protect them against oxidative degradation.

What is claimed is:

1. An article of manufacture comprising a metal object coated with a thixotropic non-carbonated magnesium-containing complex prepared by heating, at a temperature above about 30° C., a mixture comprising:
    (A) At least one of magnesium hydroxide, magnesium oxide, hydrated magnesium oxide, and a magnesium alkoxide;
    (B) At least one oleophilic organic reagent comprising a carboxylic acid, a mixture of a major amount thereof with a minor amount of a sulfonic acid or pentavalent phosphorus acid, or an ester or alkali metal or alkaline earth metal salt of either of these;
    (C) Water, if necessary to convert a substantial proportion of component A to magnesium hydroxide or hydrated magnesium oxide; and
    (D) At least one organic solubilizing agent for component B;
    the ratio of equivalents of magnesium to the acid portion of component B being at least about 5:1, and the amount of water present, if any, being at least sufficient to hydrate a substantial proportion of component A calculated as magnesium oxide.

2. An article according to claim 1 wherein component D is at least one substantially inert, normally liquid organic diluent.

3. An article according to claim 1 wherein component D is at least one substantially inert organic material which is solid at ambient temperature.

4. An article according to claim 1 wherein component D is a mixture of at least one substantially inert organic material which is solid at ambient temperature with at least one substantially inert, normally liquid organic diluent.

5. An article according to claim 3, 4 or 2 wherein component B is a mixture of at least one sulfonic acid and at least one carboxylic acid.

6. An article according to claim 5 wherein component B is a mixture of at least one alkylbenzenesulfonic acid and at least one carboxylic acid containing from about 8 to about 30 carbon atoms.

7. An article according to claim 6 wherein component A is magnesium oxide.

8. An article of manufacture comprising a metal object coated with a thixotropic non-carbonated magnesium-containing complex prepared by heating, at a temperature above about 30° C., a mixture comprising:
    (A) At least one of magnesium hydroxide, magnesium oxide, hydrated magnesium oxide, and a magnesium alkoxide;
    (B) At least one oleophilic organic reagent comprising a carboxylic acid, a mixture of a major amount thereof with a minor amount of a sulfonic acid or pentavalent phosphorus acid, or an ester or alkali metal or alkaline earth metal salt of either of these;
    (C) Water; and
    (D) At least one organic solubilizing agent for component B;
    the ratio of equivalents of magnesium to the acid portion of component B being at least about 5:1, and the amount of water present being at least sufficient to hydrate a substantial proportion of component A calculated as magnesium oxide.

9. An article according to claim 8 wherein component D is at least one substantially inert, normally liquid organic diluent.

10. An article according to claim 8 wherein component D is at least one substantially inert organic material which is solid at ambient termperature.

11. An article according to claim 8 wherein component D is a mixture of at least one substantially inert organic material which is solid at ambient temperature with at least one substantially inert, normally liquid organic diluent.

12. An article according to claim 9, 10 or 11 wherein component B is a mixture of at least one sulfonic acid and at least one carboxylic acid.

13. An article according to claim 12 wherein component B is a mixture of at least one alkylbenzenesulfonic acid and at least one carboxylic acid containing from about 8 to about 30 carbon atoms.

14. An article according to claim 13 wherein component C is present in a ratio of moles thereof to gram-atoms of magnesium in component A of at least about 0.7:1.

15. An article according to claim 14 wherein component A is magnesium oxide.

* * * * *